(12) United States Patent
Cochran et al.

(10) Patent No.: US 7,229,643 B2
(45) Date of Patent: *Jun. 12, 2007

(54) ORAL 2-METHYL-THIENO-BENZODIAZEPINE FORMULATION

(75) Inventors: George Randall Cochran, Plainfield, IN (US); Tommy Clifford Morris, Slidell, LA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/887,017

(22) Filed: Jul. 8, 2004
(Under 37 CFR 1.47)

(65) Prior Publication Data

US 2005/0085462 A1    Apr. 21, 2005

Related U.S. Application Data

(60) Continuation of application No. 09/766,218, filed on Jan. 19, 2001, now Pat. No. 6,780,433, which is a continuation-in-part of application No. 09/144,188, filed on Aug. 31, 1998, now Pat. No. 6,190,698, which is a division of application No. 08/716,922, filed on Sep. 20, 1996, now Pat. No. 5,919,485, which is a continuation-in-part of application No. 08/410,465, filed on Mar. 24, 1995, now abandoned.

(51) Int. Cl.
    *A61K 9/36*   (2006.01)
(52) U.S. Cl. .................... 424/480; 424/400; 424/464; 424/465; 424/474; 424/475; 424/479
(58) Field of Classification Search .............. 424/480, 424/482, 494, 497, 495
    See application file for complete search history.

(56) References Cited

U.S. PATENT DOCUMENTS

| 4,115,568 | A |   | 9/1978  | Chakrabarti et al. |
|-----------|---|---|---------|--------------------|
| 5,229,382 | A |   | 7/1993  | Chakrabarti et al. |
| 5,457,101 | A |   | 10/1995 | Greenwood et al. |
| 5,696,115 | A | * | 12/1997 | Rasmussen ............. 514/220 |
| 5,919,485 | A | * | 7/1999  | Cochran et al. ........ 424/480 |
| 6,780,433 | B2 | * | 8/2004 | Cochran et al. ........ 424/480 |

FOREIGN PATENT DOCUMENTS

| EP | 0 496 437 B1 |   | 7/1992 |
|----|--------------|---|--------|
| EP | 0 582 368 B1 |   | 2/1994 |
| EP | 0733367 A1   | * | 9/1996 |

OTHER PUBLICATIONS

Farmacia Practica of Remington, Second Spanish Edition, UTEHA, "Coating of tablets, capsules and pills", Mexico, (1965), pp. 505, 506 and 510.
Helman, Jose: Coating of Tablets and Related Dosage Forsm, Theoretical and Practical Pharmacotechnics, vol. VI Nov. 1982, CIA. Editorial Continental S.A. DE C.V. Mexico.
Hercules, Technical Information, Apr. 1993, "Using pure KLUCEL EF hydroxypropylcellulose to aqueous film coat tablets", pp. 1-2.
Wade A et al: Handbook of Pharmaceutical Excipients, Second Edition, 1994, pp. 355-361.
Problem Solver and Reference Manual, Presented by the Pharmaceutical Industry, FMC Corporation, 1984, pp. 1-9.

* cited by examiner

*Primary Examiner*—Michael P. Woodward
*Assistant Examiner*—Eric E. Silverman
(74) *Attorney, Agent, or Firm*—Nelsen L. Lentz

(57) ABSTRACT

The invention provides a pharmaceutically elegant solid oral formulation of olanzapine and a process for making such formulation.

1 Claim, No Drawings

ORAL 2-METHYL-THIENO-BENZODIAZEPINE FORMULATION

This is a continuation of Ser. No. 09/766,218, filed Jan. 19, 2001, now U.S. Pat. No. 6,780,433 which is a continuation-in-part application of Ser. No. 09/144,188, filed Aug. 31, 1998, now U.S. Pat. No. 6,190,698, issued Feb. 20, 2001 which is a divisional application of Ser. No. 08/716,922, filed Sep. 20, 1996, now U.S. Pat. No. 5,919,485, issued Jul. 6, 1999 which is a continuation-in-part application of Ser. No. 08/410,465 filed Mar. 24, 1995, now abandoned.

FIELD OF THE INVENTION

This invention provides an improved pharmaceutically elegant tablet formulation of 2-methyl-4-(4-methyl-1-piperazinyl)-10H-thieno[2,3-b][1,5]benzodiazepine, hereinafter referred to as olanzapine, and processess for the preparation thereof.

BACKGROUND OF THE INVENTION

The compound 2-methyl-4-(4-methyl-1-piperazinyl)-10H-thieno[2,3-b][1,5]benzodiazepine compound has useful central nervous system activity. Certain tablet formulations of olanzapine are known, as described in U.S. Pat. No. 5,229,382. However, improved oral formulations were desired in light of the moisture sensitive, polymorphic nature of olanzapine, the tendency of olanzapine to undesirably discolor in the known tablet formulation, and due to the surprisingly potent nature of olanzapine.

SUMMARY OF THE INVENTION

The presently claimed invention provides a pharmaceutically elegant solid oral formulation for comprising olanzapine intimately mixed with a bulking agent providing satisfactory hardness, friability, and disintegration time, binder, disintegrant, a dry binder to provide friability, and a lubricant; wherein such solid oral formulation is coated with polymer selected from the group consisting of hydroxypropyl methyl cellulose, hydroxyethyl cellulose, methylhydroxyethylcellulose, sodium carboxymethylcellulose, hydroxypropylcellulose, polyvinyl pyrrolidone, dimethylaminoethyl methacrylatemethylacrylate acid ester copolymer, ethylacrylate-methylmacracrylate copolymer, methylcellulose, and ethylcellulose.

A method for preparing pharmaceutically elegant, stable solid oral olanzapine formulations having a polymer coat selected from the group consisting of hydroxypropyl methyl cellulose, hydroxyethyl cellulose, methylhydroxyethylcellulose, sodium carboxymethylcellulose, hydroxypropylcellulose, polyvinyl pyrrolidone, dimethylaminoethyl methacrylatemethylacrylate acid ester copolymer, ethylacrylate-methylmacracrylate copolymer, methylcellulose, and ethylcellulose, comprised of using a high shear aqueous wet granulation with fluid bed drying process.

DETAILED DESCRIPTION OF THE INVENTION

Olanzapine, a potent compound having desired central nervous system activity has a tendency to undergo undesired polymorphic transformation, pharmaceutically undesired discoloration, and demands care to assure homogeniety of the finished solid formulation.

Applicants have discovered that olanzapine undergoes undesirable discoloration when contacted with certain excipients including powder blends. Further, the discoloration was exacerbated by ambient air conditions, at elevated temperatures, and by moist environments. Although the discoloration phenomenon does not produce in increase in the number of total related substances, the browning and mottling appearance is not generally considered pharmaceutically acceptable for commercial purposes.

Applicants have discovered that coating the solid oral formulation with a polymer selected from the group consisting of hydroxypropyl methyl cellulose, hydroxyethyl cellulose, methylhydroxyethylcellulose, sodium carboxymethylcellulose, hydroxypropylcellulose, polyvinyl pyrrolidone, dimethylaminoethyl methacrylatemethylacrylate acid ester copolymer, ethylacrylate-methylmacracrylate copolymer, methylcellulose, and ethylcellulose as a coating or subcoating provides a uniform, physical stability and effectively prevents the undesired discoloration phenomenon.

Most preferred polymer coats are hydroxypropyl methyl cellulose, hydroxypropylcellulose, methylcellulose, and ethylcellulose. An especially preferred polymer coat is hydroxypropyl methylcellulose.

Applicants have discovered that 2-methyl-4-(4-methyl-1-piperazinyl)-10H-thieno[2,3-b][1,5] benzodiazepine (olanzapine), which is a compound of the formula I:

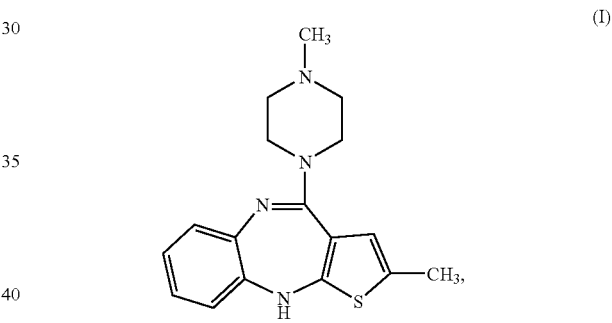

exists as two anhydrous forms which are clearly distinguishable by x-ray powder diffractometry. Unfortunately, anhydrous Form II olanzapine is metastable and is therefore not well suited for commercial use in pharmaceutical formulations. Applicants have discovered that the pharmaceutically elegant anhydrous Form I olanzapine can be formulated in its substantially pure form as a stable solid oral preparation. Such formulation provides assurance of a uniform pharmaceutically elegant product substantially free of Form II impurity in order to comply with regulatory requirements.

The Form I anhydrous 2-methyl-4-(4-methyl-1-piperazinyl)-10H-thieno[2,3-b][1,5] benzodiazepine is the most stable form of the compound; however, Applicants have discovered that the Form I anhydrous olanzapine is subject to undesired crystalline transformations in the presence of certain solvents. Further certain excipients exacerbate physical instability. For commercial pharmaceutical development and compliance with regulatory guidelines, it is important to assure that marketed formulations comprise a uniform pharmaceutically elegant substantially pure anhydrous Form I 2-methyl-4-(4-methyl-1-piperazinyl)-10H-thieno[2,3-b][1,5]benzodiazepine compound as the active ingredient and most preferably the formulation is free from undesired discolorations.

The substantially pure crystalline anhydrous Form I 2-methyl-4-(4-methyl-1-piperazinyl)-10H-thieno[2,3-b][1,5] benzodiazepine (Form I) has a typical X-ray powder diffraction pattern substantially as follows, using a Sieman's D5000 diffractometer equipped with a copper radiation source, wherein d represents the interplaner spacing:

| d | I/I$_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |
| 2.7217 | 0.20 |
| 2.6432 | 1.26 |
| 2.6007 | 0.77 |

Form II olanzapine (Form II) has a typical X-ray powder diffraction pattern substantially as follows, using a Sieman's D5000 diffractometer equipped with a copper radiation source, wherein d represents the interplaner spacing:

| d | I/I$_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns set forth herein were obtained with a copper K of wavelength=1.541A. The interplanar spacings in the column marked "d" are in Angstroms. The typical relative intensities are in the column marked "I/I$_1$". The detector was a Kevex silicon lithium solid state detector.

As used herein "substantially pure" shall refer to anhydrous Form I associated with <5% Form II; and most preferably it shall refer to <2% Form II. It is further preferred that "substantially pure" shall refer to <0.5% non-Form I polymorph.

As used herein "substantially pure" shall refer to anhydrous Form I associated with about <5% Form II; and most preferably it shall refer to about <2% Form II. It is further preferred that "substantially pure" shall refer to <0.5% related substances. When the Form I polymorph is formulated as a pharmaceutical composition, "substantially pure" shall preferably refer to about <15% Form II polymorph; more preferably, the term shall refer to about <10% Form II polymorph when the Form I polymorph is formulated as a pharmaceutical, and it is especially preferred that the term shall refer to about <5% Form II polymorph when the substantially pure substance is formulated.

As used herein, the term "2-methyl-4-(4-methyl-1-piperazinyl)-10H-thieno[2,3-b][1,5] benzodiazepine" refers to a technical grade of 2-methyl-4-(4-methyl-1-piperazinyl)-10H-thieno[2,3-b][1,5] benzodiazepine when no specific solvate or polymorph is named. Typically, the technical grade olanzapine contains less than about 5% undesired related substances and may be a mixed polymorph. Such technical grade olanzapine may contain less than about 1% undesired related substances.

The term "crude" refers to a form of olanzapine typically associated with undesired polymorph and/or greater than about 5% undesired related substances. Such crude grade olanzapine may contain less than about 1% undesired related substances.

As used herein, the term mammal shall refer to the Mammalia class of higher vertebrates. The term "mammal" includes, but is not limited to, a human. The term "treating" as used herein includes prophylaxis of the named condition or amelioration or elimination of the condition once it has been established.

The anhydrous Form I 2-methyl-4-(4-methyl-1-piperazinyl)-10H-thieno-[2,3-b][1,5] benzodiazepine compound is effective over a wide dosage range, the actual dose administered being dependent on the condition being treated. For example, in the treatment of adult humans, dosages of from about 0.25 to 50 mg, preferably from 1 to 30 mg, and most preferably 1 to 20 mg per day may be used. A once a day dosage is normally sufficient, although divided doses may be administered. For treatment of central nervous system disorders, a dose range of from 1 to 30 mg, preferably 1 to 20 mg per day is suitable. Radiolabelled Form I 2-methyl-4-(4-methyl-1-piperazinyl)-10H-thieno-[2,3-b][1,5] benzodiazepine, can be detected in the saliva and thus the compound can potentially be monitored in patients to assess compliance.

The Form I olanzapine compound is the most stable known form of olanzapine and is therefore important for the commercial development of pharmaceutical formulations which will comply with regulatory guidelines. The Form I olanzapine compound may form an undesired crystal form in the presence of certain solvents and excipients, therefore, in making the compositions of the invention it is most desired to prepare the formulation using a method which does not require dissolution of the olanzapine substance. The Form I 2-methyl-4-(4-methyl-1-piperazinyl)-10H-thieno[2,3-b][1,5] benzodiazepine compound can be converted to the less desirable polymorphic forms by contact with methylene chloride, for example. Additionally, for example, polyethylene glycol contact with the olanzapine substance produces undesired discoloration, particularly under moist conditions.

Applicants believe that a dry blend direct compression process or dry granulated processes for preparing solid oral formulations create greater opportunity for undesired poor dose uniformity. In light of the potent nature of olanzapine, consistent dose uniformity is imperative. In accordance with this invention, Applicants have discovered that a high shear aqueous wet granulation with fluid bed drying is the most effective method for preparing pharmaceutically elegant, stable, olanzapine oral formulations.

Uncoated tablets stored at ambient conditions (approximately 23° C. and 40% relative humidity) in amber, high density polyethylene bottles do not show signs of discoloration after 24 months; however, if the bottle is opened such that the tablets are exposed to open air ambient conditions then discoloration occurs within 5 days.

Applicants attempted to film coat the tablet surface to provide a more pharmaceutically elegant solid oral formulation. Groups of tablets containing 5 mg of olanzapine were coated with a clear coat (hydroxypropyl methylcellulose with polyethylene glycol), a white coat (a dry blend of ingredients comprising hydroxypropyl methyl cellulose, polyethylene glycol, polysorbate 80 and titanium dioxide dispersed in water and used an an aqueous dispersion to film coat the formulation), and a white coat with a clear coat subcoating. The coated tablets were place in bottles and stored at 40° C./75% relative humidity (RH) and 60° C. Visual evaluations indicated that the subcoated plus white coated tablets inhibited discoloration the longest period of time; however, the coated tablet characterization work indicated the the tablet coatings did not provide an acceptable solution to the discoloration problem.

The coating characterization work demonstrated that the tablet coating provided a surface barrier from air/oxygen mediated discoloration; however, the coating exacerbated the moisture related surface changes. As a result, coated tablets stored under open dish ambient conditions at low humidity showed no discoloration over extended periods of time while coated tablets stored at ambient conditions and 85% relative humidity mottled severely. Further evaluation showed that the moisture related discoloration was due to the presence of the plasticizer polyethylene glycol in the subcoating formula.

A new solid oral formulation was prepared that used a hydroxypropropyl methylcellulose subcoating and a white color coating. The new formulation did not discolor after 90 days of open dish storage at 40° C., 60° C., 40° C./75% RH, ambient temperature with 75% RH, or at ambient temperature with 85% RH. The hydroxypropyl methylcellulose coating which is free of polyethylene glycol is critical to ensure that discoloration does not occur on the tablet surface. It provides an effective barrier between the white color coat which provides an acceptable medium for imprinting and color dressing of the product. The hydroxypropylmethylcellulose coating provides sufficient barrier to prevent discoloration attributable to the polyethylene glycol in the white color coat. Alternative white film coat formulas containing alternative plasticizers were evaluated; however, none were able to prevent discoloration in all test conditions after 90 days of storage. Therefore, the hydroxypropyl methylcellulose coat or subcoating is a surprising and critical component of pharmaceutically elegant solid oral formulations of olanzapine.

A diluent or bulking agent should be selected to provide an increase in tablet size. One especially preferred diluent is lactose. Various forms of lactose are appropriate for such formulations including anhydrous, hydrous, and spray dried forms. The most desired form of lactose can be selected based on desired dissolution, content uniformity, hardness, friability, and disintegration time.

The formulation should include a binder for use in the granulation step. The artisan can choose an appropriate binder based on the acceptable viscosity, and desired hydration. Hydroxypropyl cellulose is especially preferred for use as a binder in the granulation step. The hydroxypropyl cellulose may vary in particle size. Fine grade hydroxypropyl cellulose is especially preferred for most claimed formulations.

The desired formulation includes a disintegrant for use in the granulation as well as in the running powders to facilitate the disintegration process. There are a variety of grades available, and the grade may be selected based on the acceptable batch variability. A particularly prefered disintegrant is crospovidone. A fine grade of crospovidone provides particularly desirable consistency between batches.

The artisan may choose appropriate dry binders using known methods. Such binders should be selected to assure that satisfactory friability is attained. Most preferably, dry binder is microcrystalline cellulose; however, other appropriate dry binders may be selected. Such microcrystalline cellulose may be in a granular form.

The artisan can choose an appropriate lubricant to prevent sticking and picking of the tablets to the compression tooling. One preferred lubricant is magnesium stearate.

The artisan can readily choose other appropriate aqueous dispersion film coats (color mix) for application over the hydroxypropyl methylcellulose layer. Typically, the color mixture is a dry blend of ingredients which may be dispersed in water and used as an aqueous dispersion to film coat solid formulations. One example of a typical color mixture is comprised of hydroxypropyl methylcellulose, polyethylene glycol, polysorbate 80, and titianium dioxide.

A variety of edible inks known to the artisan are appropriate for imprinting the finished formulation. For example, one typical edible ink is comprised of shellac, ethyl alcohol, isopropyl alcohol, n-butyl alcohol, propylene glycol, ammonium hydroxide, and FD&C Blue.

The solid formulation is most preferably subcoated with hydroxypropyl methylcellulose, coated with a color coat, and imprinted with an edible ink. The solid formulation may be polished using standard methods such as carnauba wax polishing, if desired.

A preferred formulation of the invention is a solid oral formulation comprising from about 1 to about 20 mg or 1 to 10 mg of active anhydrous Form I olanzapine as an effective amount of the active ingredient, provided that such solid oral formulation is coated with propyl methyl.

Most preferably, the solid oral formulation is contained in packaging materials which protect the formulation from moisture and light. For example, suitable packaging materials include amber colored high density polyethylene bottles, amber colored glass bottles, and other containers made of a material which inhibits the passage of light. Most preferably, the packaging will include a desiccant pack. The container may be sealed with an aluminum foil blister to provide the desired protection and maintain product stability.

A study of the hydroxypropyl methylcellulose sub-coated tablets in an amber colored bottle having a desiccant pack stored at harsh, 40° C./75% RH conditions for six months showed pharmaceutically acceptable stability with a 0.4% to about 1.2% increase in total related substances.

The materials for the present invention can be purchased or prepared by a variety of procedures well known to those of ordinary skill in the art. The olanzapine compound can be prepared as described by Chakrabarti in U.S. Pat. No 5,229,382 ('382), herein incorporated by reference in its entirety. It is most desirable to prepare a rapidly dissolving formulation comprising substantially pure crystalline Form I olanzapine. Such substantially pure crystalline Form I olanzapine may be prepared using the techniques described herein by the Preparation section herein infra.

As used herein mixing steps may be accomplished using common agitation methods such as stirring, shaking, and the like. As used herein the phrase "producing crystalline product from the mixture" shall refer to crystallization from the stated mixture of compound and solvent. Further, the artisan recognizes that crystallization processes may include seeding, chilling, scratching the glass of the reaction vessel, and other such common techniques.

Compound characterization methods include, for example, x-ray powder pattern analysis, thermogravimetric analysis (TGA), differential scanning calorimetery (DSC), titrametric analysis for water, and $H^1$-NMR analysis for solvent content.

The formulations were studied to assure that the Form I polymorph was substantially pure using $^{13}C$ Cross polarization/magic angle spinning (CP/MAS) NMR. Spectra were obtained using a Varian Unity 400 MHz spectrometer operating at a carbon frequency of 100.577 MHz and equipped with a complete solids accessory and Varian 5 mm or 7 mm VT CP/MAS probes. Measurement conditions were optimized for Olanzapine Form I and were as follows: 90° proton r.f. pulse 4.5 ms, contact time 1.1 ms, pulse repetition time 5 s, MAS frequency 7.0 kHz, spectral width 50 kHz, and acquisition time 50 ms. Chemical shifts were referenced to the $CH_3$ of hexamethylbenzene (d=17.3 ppm) by sample replacement. It was determined that the substantially pure Form I polymorph is retained throughout the formulation process claimed herein. Therefore, the formulations of this invention provide substantially pure Form I olanzapine polymorph in a pharmaceutically elegant formulation without producing undesired polymorphic transformation.

The following examples are provided for purposes of illustration and are not to be construed as limiting the scope of the claimed invention.

Preparation 1

Crystalline Form II Olanzapine

A 10 gram sample of crude 2-methyl-4-(4-methyl-1-piperazinyl)-10H-thieno[2,3-b][1,5] benzodiazepine was suspended in methylene chloride (100) gm and stirred at ambient temperature (20–25° C.) for a period of 1 hour. The slurry was vacuum filtered and the filtrate was recovered. The stirred filtrate was chilled to 0–5° C. in an ice bath and the solvent was slowly evaporated under a stream of nitrogen to a thick paste. Approximately ¾ of the solvent was removed by evaporation. A quantity of prechilled methylene chloride (30 gm, 0–5° C.) was mixed into the thick paste. The resulting slurry was vacuum filtered and allowed to air dry on the filter. The isolated solid was further dried in a vacuum oven at 50° C. for a period of 30 minutes. Isolated: 4.8 gm. X-ray powder characterization: Form II+$CH_2Cl_2$ Solvate.

The isolated solid was redried in a vacuum oven at 50° C. under a stream of nitrogen for a period of 30 hours. Isolated: 4.5 gm X-ray powder characterization: Form II. (described supra.)

Preparation 2

Form I Olanzapine

A sample of ethyl acetate which was saturated with technical grade 2-methyl-4-(4-methyl-1-piperazinyl)-10H-thieno[2,3-b][1,5] benzodiazepine was contacted with Form II 2-methyl-4-(4-methyl-1-piperazinyl)-10H-thieno[2,3-b][1,5]benzodiazepine (0.3 g), a seed of anhydrous Form I 2-methyl-4-(4-methyl-1-piperazinyl)-10H-thieno[2,3-b][1,5] benzodiazepine and stirred at about 25° C. for about 5 hours. The reaction product was isolated by vacuum filtration and dried under ambient conditions. Yield: 0.25 g. X-ray powder analysis indicated that the product was anhydrous Form I 2-methyl-4-(4-methyl-1-piperazinyl)-10H-thieno[2,3-b][1,5] benzodiazepine.

Preparation 3

Technical Grade olanzapine

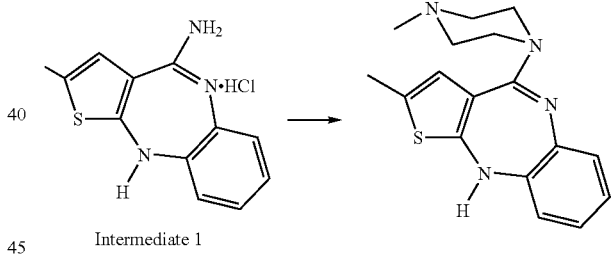

Intermediate 1

In a suitable three neck flask the following was added:
Dimethylsulfoxide (analytical): 6 volumes
Intermediate 1: 75 g
N-Methylpiperazine (reagent): 6 equivalents Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until • 5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

Yield: 76.7%; Potency: 98.1%

The procedure of Preparation 3 was repeated substantially as described above and provided a yield of 81% with a potency of 101.1%.

Preparation 4

Technical Grade Olanzapine

Intermediate 1 (supra) was suspended in DMSO (3.2 vol.) and toluene (4.5 vol.). A portion (•0.65 vol.) of the solvent was removed by distillation at 120–125° C. The mixture was cooled to 110° C., N-methylpiperazine(NMP, 4.2 equiv.) was added and the mixture heated back to reflux (120–125° C.). Another portion (•1 vol.) of the solvent was removed by distillation to dry the reaction mixture. A vigorous reflux was desired to drive the reaction to completion (about 7 hrs.) by removing ammonia from the reaction. The product was isolated by the slow addition of water (12.75 vol.) to the cooled (10° C.) reaction solution. The product was collected by filtration and washed with chilled water (2 vol.). The crude olanzapine was dried in vacuo at 60° C. The product was recrystallized from hot toluene (5 vol.) to give a technical grade olanzapine. After drying in vacuo at 50° C., the technical grade olanzapine was recrystallized again from ethyl acetate (10 vol.)/toluene (0.62 vol.)/methanol (3.1 vol.) to give olanzapine as a methanol solvate. The methanol solvate upon drying at >50° C. was converted to an anhydrous technical grade olanzapine.

Preparation 5

Form I From Acetone

A 3.0 g sample of technical grade 2-methyl-4-(4-methyl-1-piperazinyl)-10H-thieno[2,3-b][1,5] benzodiazepine was suspended in acetone (30 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5] benzodiazepine using x-ray powder analysis. Yield: 0.8 g.

Preparation 6

Form I Using Tetrahydrofuran

An 8.0 g sample of technical grade 2-methyl-4-(4-methyl-1-piperazinyl)-10H-thieno[2,3-b][1,5] benzodiazepine was suspended in tetrahydrofuran (25 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1, 5]benzodiazepine using x-ray powder analysis. Yield: 1.3 g.

Preparation 7

Form I Using Ethyl Acetate

A 270 g sample of technical grade 2-methyl-4-(4-methyl-1-piperazinyl)-10H-thieno[2,3-b][1,5] benzodiazepine was suspended in ethyl acetate (2.7 L). The mixture was heated to about 76° C. and maintained at about 76° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5] benzodiazepine using x-ray powder analysis.

Yield: 197 g.

Preparation 8

Form I From t-butanol

A 1.0 g sample of technical grade 2-methyl-4-(4-methyl-1-piperazinyl)-10H-thieno[2,3-b][1,5] benzodiazepine was suspended in tert-butanol (30 g). The stirred mixture was heated to about 60° C. and maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5] benzodiazepine using x-ray powder analysis.

Yield: 0.3 g.

Preparation 9

Form I from Slurry Conversion of Form II in Toluene

A 0.5 g sample of technical grade 2-methyl-4-(4-methyl-1-piperazinyl)-10H-thieno[2,3-b][1,5] benzodiazepine and a 0.5 g sample of Form II 2-methyl-4-(4-methyl-1-piperazinyl)-10H-thieno[2,3-b][1,5] benzodiazepine were suspended in toluene (5 ml), presaturated with 2-methyl-4-(4-methyl-1-piperazinyl)-10H-thieno[2,3-b][1,5] benzodiazepine. The mixture was stirred in a sealed vial at about ambient temperature for about 22 hours. The resulting product was isolated using vacuum filtration and dried under vacuum at about 45° C. The product was identified as Form I 2-methyl-4-(4-methyl-1-piperazinyl)-10H-thieno[2,3-b][1, 5] benzodiazepine using x-ray powder analysis.

EXAMPLE 1

A portion of the hydroxypropyl cellulose was dissolved in purified water to form a solution for granulation. The remaining hydroxypropyl cellulose (total of 4.0% w/w final tablet weight), which was an extra fine grade, was combined with the olanzapine (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The running powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating:

Hydroxypropyl methylcellulose (10% w/w) was mixed with purified water to form a solution. Core tablets were divided into approximately equal sections and spray coated with the hydroxypropyl methylcellulose solution. The operation was performed in a perforated coating pan.

Coating of Core Tablets:

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

EXAMPLE 2

The process substantially as described above in Example 1 was repeated using the following ingredients to provide pharmaceutically elegant tablet formulations containing 1, 2.5, 5, 7.5, and 10 mg olanzapine, respectively, per tablet:

1 mg Olanzapine per Tablet:

| Names of Ingredients | Quantity (mg/tablet) |
|---|---|
| Active Ingredient | |
| Olanzapine | 1.0 |
| Other Ingredients | |
| Lactose | 67.43 |
| Hydroxypropyl Cellulose | 3.40 |
| Crospovidone | 4.25 |
| Microcrystalline Cellulose | 8.50 |
| Magnesium Stearate | 0.42 |
| Subcoating | |
| Hydroxypropyl Methylcellulose Coating | 1.70 |
| Color Mixture White Polishing | 3.47 |
| Carnauba Wax Imprinting | trace |
| Edible Blue Ink | trace |

Olanzapine 2.5 mg Tablets

| Names of Ingredients | Quantity (mg/tablet) |
|---|---|
| Active Ingredient | |
| Olanzapine | 2.5 |
| Other Ingredients | |
| Lactose | 102.15 |
| Hydroxypropyl Cellulose | 5.20 |
| Crospovidone | 6.50 |
| Microcrystalline Cellulose | 13.00 |
| Magnesium Stearate | 0.65 |
| Subcoating | |
| Hydroxypropyl Methylcellulose Coating | 2.60 |
| Color Mixture White Polishing | 5.30 |
| Carnauba Wax Imprinting | trace |
| Edible Blue Ink | trace |

Olanzapine 5.0 mg Tablets

| Names of Ingredients | Quantity (mg/tablet) |
|---|---|
| Active Ingredient | |
| Olanzapine | 5.00 |
| Other Ingredients | |
| Lactose | 156.00 |
| Hydroxypropyl Cellulose | 8.00 |
| Crospovidone | 10.00 |
| Microcrystalline Cellulose | 20.00 |
| Magnesium Stearate | 1.00 |
| Subcoating | |
| Hydroxypropyl Methylcellulose Coating | 4.00 |
| Color Mixture White Polishing | 8.16 |
| Carnauba Wax Imprinting | trace |
| Edible Blue Ink | trace |

Olanzapine 7.5 mg Tablets

| Names of Ingredients | Quantity (mg/tablet) |
|---|---|
| Active Ingredient | |
| Olanzapine | 7.50 |
| Other Ingredients | |
| Lactose | 234.00 |
| Hydroxypropyl Cellulose | 12.00 |
| Crospovidone | 15.00 |
| Microcrystalline Cellulose | 30.00 |
| Magnesium Stearate | 1.50 |
| Subcoating | |
| Hydroxypropyl Methylcellulose Coating | 6.00 |
| Color Mixture White | 12.24 |

| Names of Ingredients | Quantity (mg/tablet) |
|---|---|
| Polishing | |
| Carnauba Wax | trace |
| Imprinting | |
| Edible Blue Ink | trace |

Olanzapine 10.0 mg Tablets

| Names of Ingredients | Quantity (mg/tablet) |
|---|---|
| Active Ingredient | |
| Olanzapine | 10.00 |
| Other Ingredients | |
| Lactose | 312.00 |
| Hydroxypropyl Cellulose | 16.00 |
| Crospovidone | 20.00 |
| Microcrystalline Cellulose | 40.00 |
| Magnesium Stearate | 2.00 |
| Subcoating | |
| Hydroxypropyl Methylcellulose | 8.00 |
| Coating | |
| Color Mixture White | 16.32 |
| Polishing | |
| Carnauba Wax | trace |
| Imprinting | |
| Edible Blue Ink | trace |

The invention claimed is:

1. A solid oral formulation comprising olanzapine wherein the solid oral formulation is coated with a polymer which is hydroxypropyl methylcellulose wherein the polymer coating is free of polyethylene glycol.

* * * * *